United States Patent
Perone

(10) Patent No.: US 7,014,642 B1
(45) Date of Patent: Mar. 21, 2006

(54) OBSTETRICAL FORCEPS WITH PULL-SENSING HANDLE GRIP

(76) Inventor: Nicola Perone, 8827 Memorial Dr., Houston, TX (US) 77024

( * ) Notice: Subject to any disclaimer, the term of this patent is extended or adjusted under 35 U.S.C. 154(b) by 0 days.

(21) Appl. No.: 10/455,910

(22) Filed: Jun. 6, 2003

(51) Int. Cl.
 *A61B 17/42* (2006.01)
(52) U.S. Cl. ...................................... 606/122
(58) Field of Classification Search ............... 606/205, 606/110, 119–124, 127, 34, 37, 38, 41, 42, 606/51, 52, 211; 128/774
 See application file for complete search history.

(56) References Cited

U.S. PATENT DOCUMENTS

| | | | |
|---|---|---|---|
| 3,665,925 A | | 5/1972 | Dersookian |
| 3,785,381 A | | 1/1974 | Lower et al. |
| 4,534,424 A | * | 8/1985 | Ramsey ..................... 175/40 |
| 4,858,620 A | * | 8/1989 | Sugarman et al. .......... 600/587 |
| 5,047,046 A | * | 9/1991 | Bodoia ....................... 606/205 |
| 5,649,934 A | * | 7/1997 | Smeltzer et al. ........... 606/122 |
| 6,080,106 A | * | 6/2000 | Lloyd et al. ............... 600/300 |
| 6,186,962 B1 | * | 2/2001 | Lloyd et al. ............... 600/587 |
| 6,361,542 B1 | * | 3/2002 | Dimitriu et al. ........... 606/123 |
| 6,409,636 B1 | * | 6/2002 | Risso et al. ................. 482/82 |
| 6,425,899 B1 | * | 7/2002 | Biehl ......................... 606/122 |
| 6,440,070 B1 | * | 8/2002 | Israel ......................... 600/398 |

OTHER PUBLICATIONS

Wylie, B.: Traction in Forceps Deliveries. Am. J. Obstet. & Gynecol. 29:425, 1935.
Baxter, J.: The Obstetrical Forceps: Controlled Axis Traction. J. Obstet. Gynec. Brit. Emp. 53:42, 1946.
Fleming, A.R., Brandeberry, K.R., and Pearse, W.H.: Introduction of a Metric Forceps. Am. J. Obstet. & Gynecol. 78:125, 1959.

* cited by examiner

*Primary Examiner*—Kevin T. Truong
(74) *Attorney, Agent, or Firm*—Raymond R. Ferrera; Arnold & Ferrera, L.L.P.

(57) ABSTRACT

The invention consists of an obstetrical forceps with a pull-sensing handle grip containing electronic hardware, whose purpose is to reduce the risk of injury to the fetus and mother caused by excessive traction force. The hardware includes a strain gauge to measure the traction force applied to the forceps during a delivery, an announcer to alert the doctor when the traction force exceeds preset safety limits, and a transceiver for the wireless transmission of the traction data to a receiver connected to a lap-top computer, which generates a graphic representation of such data.

13 Claims, 4 Drawing Sheets

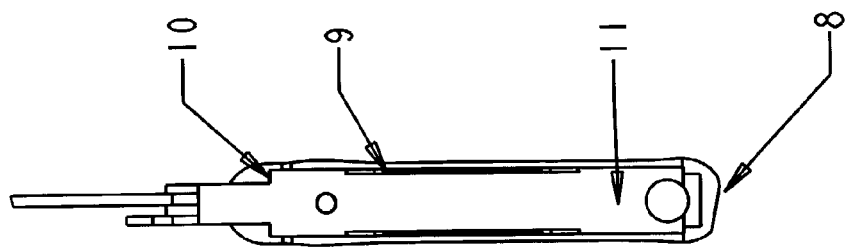
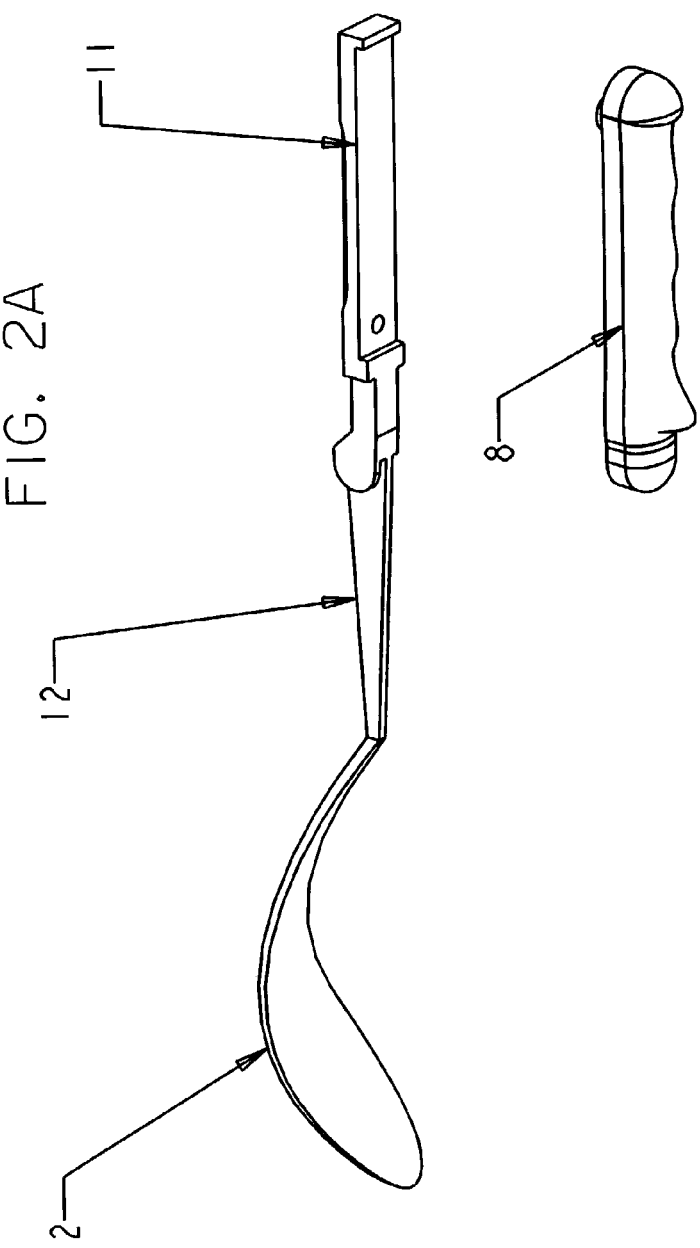

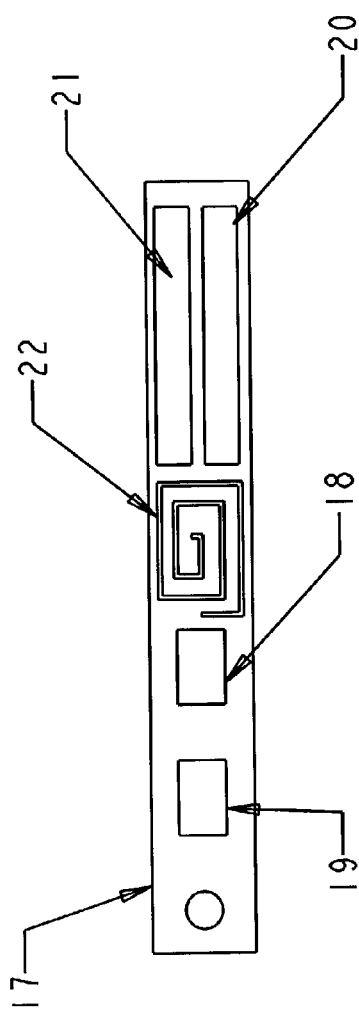
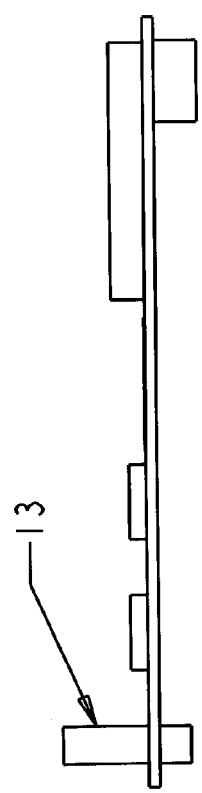
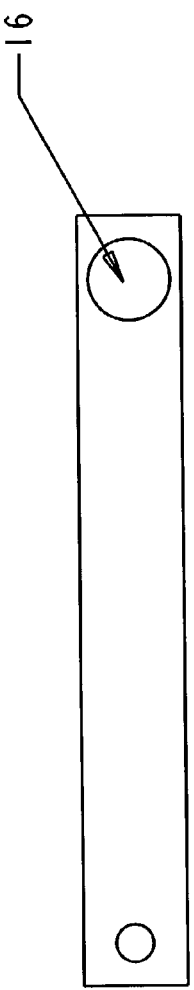
FIG. 4A
FIG. 4B
FIG. 4C

OBSTETRICAL FORCEPS WITH PULL-SENSING HANDLE GRIP

FIELD OF THE INVENTION

This invention pertains to devices for assisting in the delivery of a baby. Specifically, the present invention relates to an obstetrical forceps with a pull-sensing handle grip, containing electronic hardware whose purpose is to measure the traction force used during a delivery, to alert the doctor when such a force exceeds safety limits, and to enable the wireless transmission of the traction force data to a receiver connected with a lap-top computer.

BACKGROUND OF THE INVENTION

Obstetrical forceps are medical instruments comprised of two blades (i.e. the fetal head engaging portions), each connected to a handle by a shank, with a sliding lock between the handle and the shank. The forceps typically grasp the fetal head in a tong-like manner and are used for assisting in the delivery of a baby. When needed, they can be a valuable medical tool to shorten or end the second (expulsion of the fetus) stage of labor, whenever to do so is in the best interest of the mother or the fetus.

Despite the remarkable evolution of this instrument since its introduction in the 1600's, little progress has been made in avoidance of excessive traction forces, in order to prevent injury to the fetal head during a delivery. In fact, when to desist from further extractive efforts is left to the judgment and courage of the obstetrician. Consequently, there is always the risk of a traction force being applied to the forceps that exceeds the limits of safety, with severe head trauma to the baby, resulting in complications ranging from perinatal death, cerebral palsy, and neurological disorders, to mental retardation and behavioral problems.

The above devastating consequences of excessive pull during a forceps delivery, and the resulting medico-legal sequelae, have prompted several attempts over the years to develop devices to measure the compression and traction forces applied to the fetal head during the use of forceps.

Examples of such forceps include U.S. Pat. No. 3,665,925, related to an obstetrical forceps that mechanically indicate the pressure exerted to the fetal head through strain gauges applied to the base of the forceps; U.S. Pat. No. 3,785,381, related to an obstetrical forceps with a pressure sensor arranged on the tip of the fetal engaging portion of the blade; and U.S. Pat. No. 5,649,934, related to an obstetrical forceps with sensing optical bending strains embedded in the shanks. All the above modifications have inherent drawbacks. In particular, the previous inventions are cumbersome and time-consuming to use, which makes it unlikely for a doctor to resort to them, particularly during an emergency delivery. In fact, some of them require calibration prior to their use (U.S. Pat. No. 5,649,934), while others have sensors taped to the blades, gauges attached to the handles, and fastidious cable connections. In addition, these previous inventions may pose problems with sterilization.

Accordingly, there is a need for improved obstetrical forceps that can measure the traction forces applied to the fetal head without the constraints and design drawbacks seen in the prior art and described above.

SUMMARY OF THE INVENTION

The invention consists of an obstetrical forceps with a pull-sensing handle grip containing electronic hardware whose purpose is to measure the traction force applied to the fetal head during a delivery, to set off an audible signal when such a force exceeds preset safety limits, and to transmit in a wireless fashion, the traction force data to a receiver connected with a lap-top computer.

A novel feature of this invention is the easy adaptability of the pull-sensing handle grip to any forceps, not just to the Elliot type of forceps shown in the drawings, but to other classic and special type of forceps, without having to change the basic design of the blades or shanks, which have been accepted for years as standard in obstetrics. This easy adaptability makes it unnecessary to discard one's favorite forceps. Another novel feature is the elimination of cumbersome cable connections between the strain gauge and the sounder, and between the transceiver and the receiver, which can interfere with the forceps application. Still another novel feature of this invention is the graphic representation of the pull applied to the forceps throughout the delivery, useful for research purposes or in case of medical malpractice litigation. A further feature of this invention is that the electronic handle grip assembly can be either disposed after a single use, or it can be easily sterilized for reuse, without significant impact on materials or functionality.

The foregoing has outlined rather broadly the features and technical advantages of the present invention so that the detailed description of the invention that follows may be better understood. Additional features and advantages of the invention will be described hereinafter, which form the subject of the invention. It should be appreciated by those skilled in the art that the conception and the specific embodiments disclosed might be readily used as a basis for modifying or designing other obstetrical forceps with pull-sensing handle grips for carrying out the same purposes of the present invention. It should also be realized by those skilled in the art that such equivalent constructions do not depart from the spirit and scope of the invention as set forth herein.

BRIEF DESCRIPTION OF THE DRAWINGS

The accompanying drawings, which are incorporated in and form a part of the specification, illustrate the embodiments of the present invention, and, together with the description, serve to explain the principles of the invention. In the drawings:

FIG. 2A is a perspective view of the left forceps blade, shank, and handle properly modified to allow nesting of the handle grip assembly, which is shown in its external view (FIG. 2B) and cross-sectional view (FIG. 2C);

FIGS. 4A, 4B, and 4C are a top, side, and bottom view of a printed circuit board of the present invention, showing a strain gauge, a microprocessor chip, a transceiver chip, a radio-frequency antenna, a rechargeable battery, and a field coil recharger.

It is to be noted that the drawings illustrate only typical embodiments of the invention and are therefore not to be considered limiting of its scope, for the invention will admit to other equally effective embodiments.

DETAILED DESCRIPTION OF THE INVENTION

Figure 1:
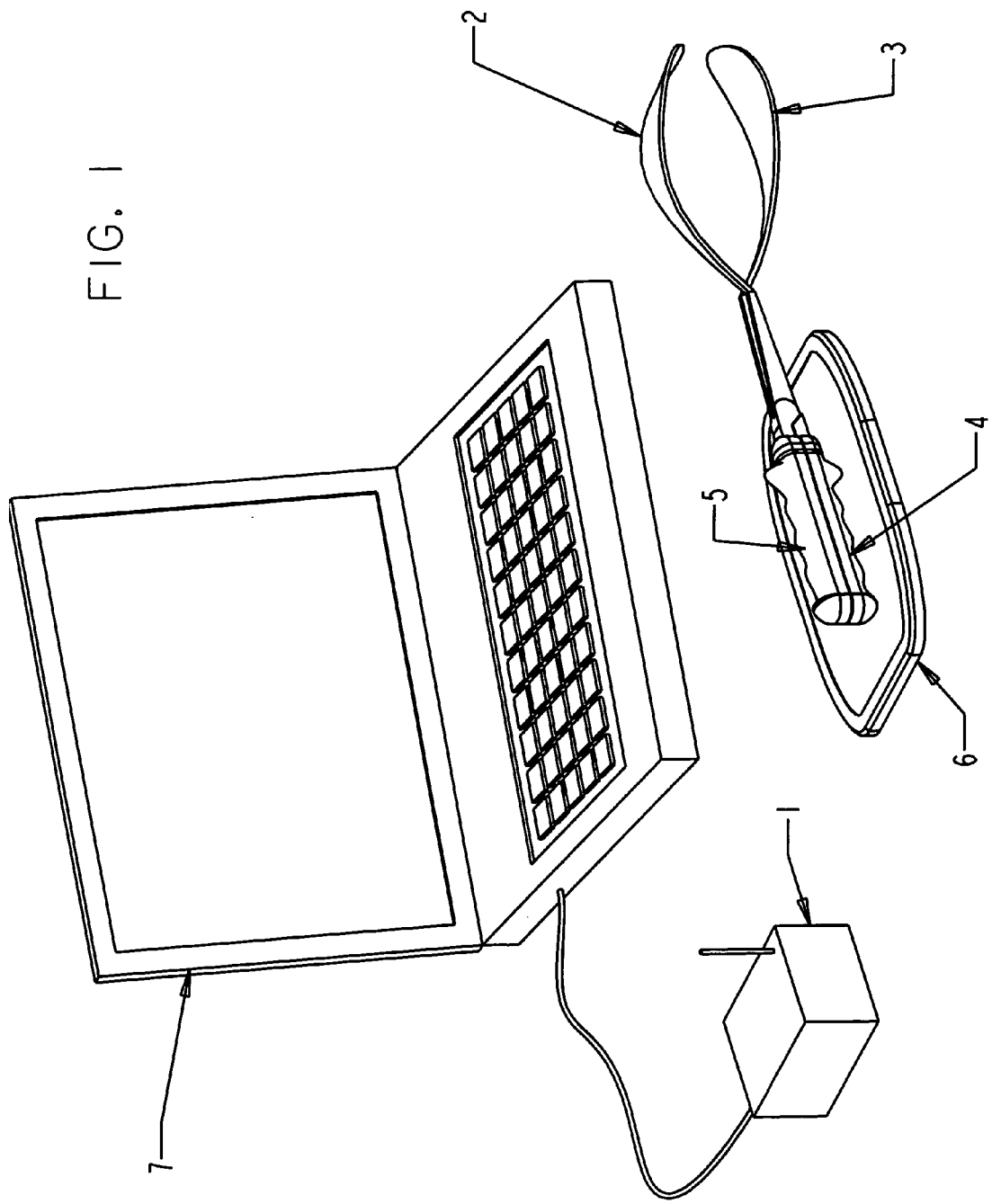
FIG. 1 shows an obstetrical forceps with a pull-sensing handle grip assembly in place, resting on a recharge pad, and a radio receiver connected to a lap-top computer.

Turning now to FIG. 1, there is shown obstetrical forceps having a pull-sensing handle grip of the present invention. While many different types of forceps made of different materials have been described and developed throughout time, they consist principally of the following four major components:

(A) Blades—(2) and (3): Each blade has two curves. The blades can be oval or elliptical and can be fenestrated or solid with smooth surfaces and edges, in order to reduce damage to the soft tissues when applied to the fetal head. They have a cephalic curve to allow a firm grasp of the fetal head.

(B) Shanks: These connect the blades to the handles and provide the length of the device. They are either parallel or crossing and are often made of stainless steel.

(C) Lock: Many different types have been designed. The lock is the type of articulation between the shanks.

(D) Handles—(4) and (5): These are the location where the doctor holds the forceps device and applies traction to the fetal head. Here, both of the forceps handles have been modified such that a pull-sensing handle grip assembly may be snapped into place. The handles (4) and (5) contain the radio transmitter discussed below.

As discussed in more detail below, the pull-sensing handle grip assembly of the present invention contains electronic hardware whose purpose is to measure the traction force applied to the fetal head during a delivery; to set off an audible signal when such a force exceeds preset safety limits; and, to transmit in a wireless fashion, the traction data to a receiver connected to a lap-top computer.

In FIG. 1, the obstetrical forceps rest on a recharging pad (6) used to inductively recharge the power supply or batteries housed within both of the handle grips (4) and (5). As also seen in FIG. 1, a radio receiver (1) is connected with a lap-top computer (7), which displays and records the traction data transmitted by the grip assembly and generates a graphic recording, which can be stored, analyzed, processed, or otherwise made part of the patient's hospital medical record.

Turning now to FIG. 2A, there is shown a blade (2), shank (12), and handle (11) of one side of the forceps. The handle (11) has been recessed or modified to allow for nesting of the grip assembly (8), which is shown in its external (FIG. 2B) and cross-sectional (FIG. 2C) views. In particular, the grip assembly (8) can be detachably secured to the handle (11). The grip/handle tab area (9) allows the grip assembly (8) to snap over the handle (11) for positive retention and the grip/handle nest profiles (10) eliminate fore/aft and side-to-side translations. While only one handle grip assembly is depicted in FIGS. 2B and 2C, the forceps used according to the present invention includes two pull-sensing handle grip assemblies for data redundancy or for monitoring and identifying more dynamic loading conditions. In any event, the handle grip portions of the forceps can be provided with the usual contoured finger gripping surfaces for facilitating gripping by hand.

Figure 3:
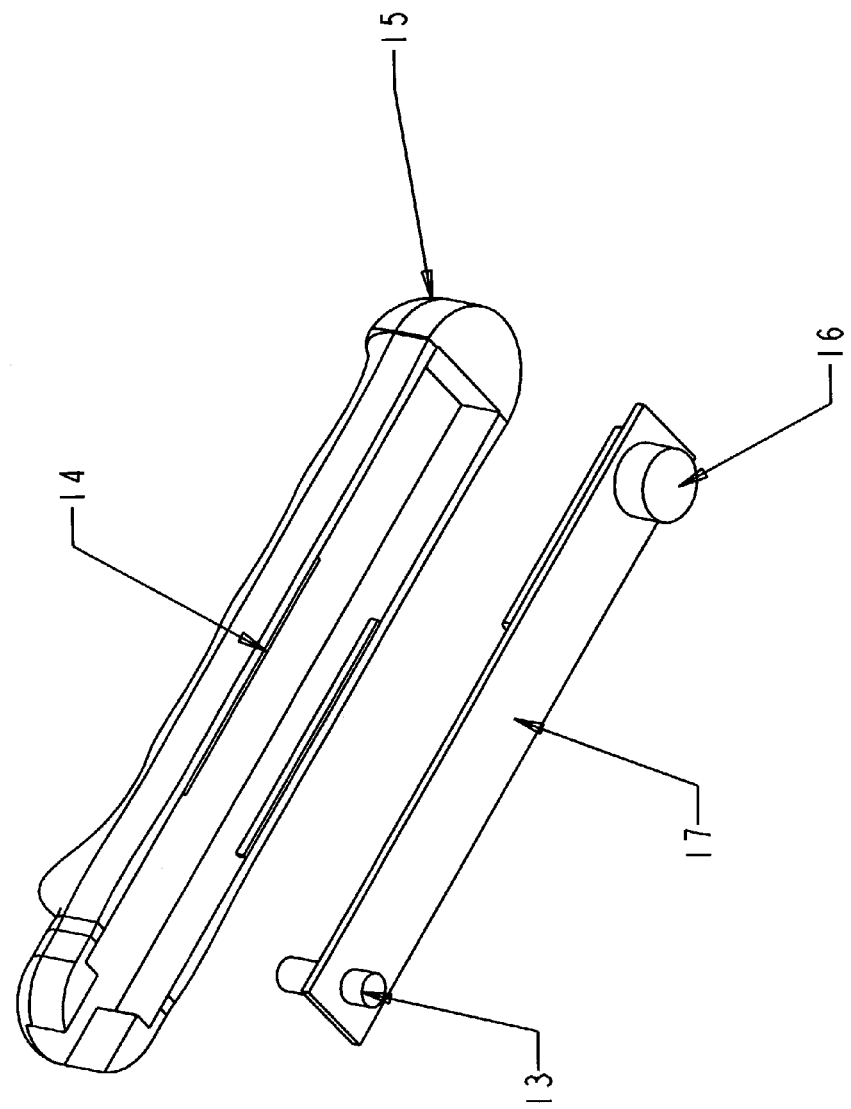
FIG. 3 is an exploded perspective view of the snap-on, plastic, handle grip housing and the printed circuit board assembly.

FIG. 3 is an exploded perspective view of the snap-on, plastic, handle grip housing and printed circuit board assembly discussed above. When assembled, the pull-sensing handle grip housing houses the printed circuit board (PCB) assembly (17), whose purpose is to measure the traction force applied to the forceps, to transmit data, and to control the power envelope. The circuit board (17) is potted into the handle using known manufacturing techniques. More specifically, a grip tab (14) allows the grip assembly to snap over the handle for positive retention while a grip housing (15), which is injection molded, houses the radio transmitter, strain gauge, and printed circuit board. As such, the circuit card is encapsulated within the grip housing (15).

In particular, FIGS. 4A, 4B, and 4C illustrate a top, side, and bottom view of a PCB assembly of the present invention, showing a strain gauge (13), a microprocessor chip (19), a transceiver chip (18), a radio-frequency antenna (22), a rechargeable battery (21), and a field coil recharger (20).

In particular, the strain gauge (13) measures the traction force between the grip assembly and the forceps shank. While any range of force may be measured, the typical range of force is 0 to 100 pounds of force in a delivery. While there are several methods of measuring strain, the most common is with a strain gauge, such as a resistive strain gauge. When a force is applied to a structure, the length of the structure changes. Strain is the ratio of this change in dimension to the original, and strain gauges are used to measure it. As the strain gauge is glued to the structure (such as the rod shown in FIG. 4B), any distortion will also cause a distortion of the strain gauge. The gauge contains semi-conducting material and the distortion therefore results in a change in its resistance. By measuring this change in resistance, one can measure the strain. As such, a strain gauge's electrical resistance varies in proportion to the amount of strain placed on it.

The microprocessor chip (19) controls the functions of the grip assembly. While many different microprocessors known in the art can be used, the preferred chip is an 8-bit chip with sufficient RAM data storage.

The transceiver chip (18) controls radio communications between the grip assembly and radio receiver (1). The preferred transceiver chip is a digital chip that can transmit the desired strain gauge data to the receiver. While any analog or digital radio frequency (RF) or infrared frequency (IF) spectrum communication system is contemplated, any kind of wireless system now known (or to be known) in the art can be used with this device, including Bluetooth wireless technology.

The rechargeable battery (21) provides power during forceps use. As is known to those skilled in the art, popular rechargeable batteries include NiCd and NiMH batteries. If desired, a disposable, non-rechargeable battery such as an alkaline battery can be used.

The field coil recharger (20) provides recharging power to the battery (21) when forceps grip rests on the recharging pad (6). The preferred field coil recharger that is used is known as a "near-field" field coil recharger.

The speaker (16) creates an audible warning alarm when a preset traction force limit has been reached. How much force to be applied to the forceps in order to complete a delivery depends on such factors as the number of babies previously borne by the mother and the size and weight of the baby. Of course, instead of an audible alarm signal, the device could be constructed to provide a visual alarm signal or other signal. Because of the size of the device, a micro-speaker is preferred.

The radio frequency antenna (22) relates data between the handle grip assembly and the receiver. In general, any kind of radio frequency antenna system for a wireless infrastructure can be used, for example, a digital high frequency antenna can be used.

In operation, with the parts assembled as indicated in FIGS. 3 and 4, the doctor snaps the pull-sensing handle grip assemblies into place on the handles of the forceps, positions the forceps about the head of the baby, and exerts a pulling force on the handles to aid in the delivery of the baby. Through the wireless technology described herein, the doctor is able to accurately and safely gauge the amount of pull exerted on the baby's head by the forceps, thereby preventing damage to the baby and mother.

As described herein, the present invention obviates the problems of the prior art by providing an obstetrical forceps with a pull-sensing handle grip that is simply snapped on just before use. Thus, it is quickly assembled and does not require cable connections and sensors in the shanks or blades, which could interfere with their application on the fetal head. The snap-on, pull-sensing handle grip, which can be adapted to all types and shapes of forceps, contains all the electronic hardware necessary to accurately measure the traction force, to alert in real-time the doctor when such a force exceeds preset safety limits, and to enable the wireless transmission of the traction force data to a receiver connected with a lap-top computer. In this fashion, a graphic representation can be generated of the traction force applied during the delivery, which can be useful for research purposes or can be presented in case of medical malpractice litigation, as evidence that safety limits were not exceeded.

In addition, as far as sterilization is concerned, the handle grip assembly can be provided already sterile and disposed after a single use, thus limiting the need for sterilization only to the metal portion of the forceps, through routine autoclave pressure method. On the other hand, the handle grip, in its re-usable version, can be easily sterilized without any damage to the electronic hardware, either through a low temperature sterilization process (such as the STIRRAD method), or, alternatively, by immersion in a sterilizing solution (such as CIDEX). In fact, the printed circuit board is encapsulated within the plastic grip with epoxy compound, thus it is impervious to immersion in a liquid disinfectant.

Although the present invention and its advantages have been described in detail, it should be understood that various changes, substitutions, and alterations could be made herein without departing from the spirit and scope of the invention as defined by the appended claims.

What is claimed is:

1. An obstetrical forceps system for assisting in the delivery of a fetus, said system comprising:

an obstetrical forceps having a first member, said first member having a blade end, a shank, and a handle end, wherein said handle end is equipped with a detachably disposed first handle grip assembly; and a second member, said second member having a blade end, a shank, and a handle end, wherein said handle end is equipped with a detachably disposed second handle grip assembly; wherein said first member and said second members are mutually connected by means of a sliding lock disposed between said blade ends and said handle ends;

a means for electronically measuring the traction forces exerted on a fetal head, wherein said means is disposed in at least one of said first handle grin assembly and said second handle grip assembly; and a means for transmitting a signal representative of measured traction forces.

2. The obstetrical forceps system of claim 1, further comprising a receiver for receiving said signal representative of measured traction forces.

3. The obstetrical forceps system of claim 2, wherein said receiver further comprises a means for graphically said measured traction forces.

4. The obstetrical forceps system of claim 3, wherein said receiver further comprises a video monitor.

5. The obstetrical forceps system of claim 2, wherein said receiver for receiving said signal representative of measured traction forces further comprises a wireless receiver.

6. The obstetrical forceps system of claim 3, wherein said means for graphically representing said measured traction forces further comprises a lap top computer.

7. The obstetrical forceps system of claim 1, wherein said means for electronically measuring traction forces exerted on a fetal head further comprises a strain gauge.

8. The obstetrical forceps system of claim 7, further comprising a battery-powered strain gauge.

9. The obstetrical forceps system of claim 1, wherein said means for transmitting a signal representative of said measured traction forces is further comprises a wireless transmitter.

10. The obstetrical forceps system of claim 1, further comprising:

a means for generating an alarm when said traction forces exceed a predetermined level.

11. The obstetrical forceps system of claim 10, wherein said means for generating an alarm is further comprises a speaker.

12. The obstetrical forceps system of claim 11, wherein said speaker is disposed in said first handle grip assembly.

13. The obstetrical forceps system of claim 11, wherein said speaker is disposed in said second handle grip assembly.

* * * * *